(12) United States Patent
Birkner et al.

(10) Patent No.: US 7,273,587 B1
(45) Date of Patent: Sep. 25, 2007

(54) RAPID TISSUE PROCESSING METHOD AND APPARATUS

(75) Inventors: Jeffrey C. Birkner, Bloomfield, IA (US); Michael L. Woltman, Ottumwa, IA (US)

(73) Assignee: Collaborative Laboratory Services, LLC, Bloomfield, IA (US)

( * ) Notice: Subject to any disclaimer, the term of this patent is extended or adjusted under 35 U.S.C. 154(b) by 0 days.

(21) Appl. No.: 10/904,892

(22) Filed: Dec. 2, 2004

(51) Int. Cl.
*B32B 5/02* (2006.01)

(52) U.S. Cl. .......................... 422/63; 422/62; 422/65; 422/99; 422/100; 422/104; 435/40.5

(58) Field of Classification Search .......... 422/50–101, 422/104; 436/180; 435/40.5
See application file for complete search history.

(56) References Cited

U.S. PATENT DOCUMENTS

| | | | |
|---|---|---|---|
| 3,961,097 A | 6/1976 | Gravlee | |
| 4,247,594 A | 1/1981 | Shea et al. | |
| 4,569,647 A | 2/1986 | McCormick | |
| 4,656,047 A | 4/1987 | Kok et al. | |
| 4,839,194 A | 6/1989 | Malluche et al. | |
| 5,023,187 A | 6/1991 | Koebler et al. | |
| 5,089,288 A | 2/1992 | Berger | |
| 5,244,787 A | 9/1993 | Key et al. | |
| 5,344,637 A | 9/1994 | Camiener | |
| 6,042,874 A | 3/2000 | Visinoni et al. | |
| 6,207,408 B1 | 3/2001 | Essenfeld et al. | |
| 6,291,180 B1 | 9/2001 | Chu | |
| 6,451,551 B1 | 9/2002 | Zhan et al. | |
| 6,555,389 B1 * | 4/2003 | Ullman et al. | 436/514 |
| 6,586,713 B2 | 7/2003 | Essenfeld et al. | |
| 6,793,890 B2 | 9/2004 | Morales | |
| 2002/0177183 A1 | 11/2002 | Giberson et al. | |
| 2003/0044853 A1 * | 3/2003 | Socks et al. | 435/7.9 |
| 2003/0175947 A1 * | 9/2003 | Liu et al. | 435/288.5 |

FOREIGN PATENT DOCUMENTS

EP 0822403 2/1998

OTHER PUBLICATIONS

L. P. Kok, P. E. Visser, M. E. Boon; Histoprocessing with Microwave oven: an update; Histochemical Journal 20, 323-328 (1988).
L. Ralph Rohr, MD, Lester J. Layfield. MD, Deborah Wallin, HT(ASCP), Denise Hardy, HT (ASCP): A Comparison of Routine and Rapid Microwave Tissue Processing in a Surgical Pathology Laboratory; Am J Clin Pathol 2001; 115:703-708.
Anthony S-Y. Leong; Review Article: Microwave Technology for Morphological Analysis; Cell Vision; vol. 1, No. 4 (1994)1278-288.

(Continued)

*Primary Examiner*—Jill Warden
*Assistant Examiner*—Jyoti Nagpaul
(74) *Attorney, Agent, or Firm*—Ryan N. Carter

(57) ABSTRACT

A rapid tissue processing method and apparatus including the steps of fixation, dehydration, clearing, and impregnation. The preferred method is performed in a processing unit that employs alternating microwave and ohmic energy to heat the process solution and tissue sample. In one embodiment, the method employs environmentally friendly green chemicals to effectuate the processing.

12 Claims, 6 Drawing Sheets

OTHER PUBLICATIONS

Leonard et al. A Comparison of Heating Modes in Rapid Fixation Techniques for Electron Microscopy; The Journal of Histochemistry and Cytochemistry, vol. 42, No. 3 (1994) pp. 383-391.

Stelly et al. Mayer's Hemalum-Methyl Salicylate: A Stain-Clearing Technique for Observations Within Whole Ovules; Stain Technology, vol. 59, No. 3 (1984) pp. 155-161.

* cited by examiner

RAPID TISSUE PROCESSING METHOD AND APPARATUS

BACKGROUND OF THE INVENTION

The present invention relates to tissue processing, and more particularly it relates to a rapid tissue processing method and apparatus that uses ohmic energy and microwave energy to heat the process solution and tissue sample during processing. The present invention also relates to a tissue processing method that employs the use of environmentally friendly green chemicals.

A tissue sample must be processed before it can be analyzed for diagnostic or testing purposes. This processing acts to halt the degradation of cellular structure, and to stabilize the cellular characteristics, and to sufficiently harden the tissue so that extremely fine segments may be cut therefrom for purposes of analysis. Tissue processing is well known in the art of histology.

There are four general steps performed when processing a tissue sample: fixation, dehydration, clearing, and impregnation (sometimes herein also referred to as infiltration). These steps are generally effectuated by submerging the tissue sample in different solutions to produce chemical reactions. It is important that tissue samples be processed in a quality and uniform manner so that the analytical results and diagnosis are consistent and accurate. Some of the types of analysis that can be performed on tissue samples after the sample has been processed include visual analysis, gel electrophoresis, immunohistochemical stains, flow cytometry, and other genetic analysis. Physicians diagnose a variety of ailments and diseases based upon these analyses.

Fixation initiates preservation of the tissue specimen by cross linking proteins and halting cellular degradation. Without chemical fixation, endogenous enzymes will catabolize and lyse the cell, and the cellular microanatomy will be altered. Traditionally, fixatives have included ketones, aldehydes, alcohols, acetic acid, heavy metals, chromic acid, picric acid, or osmium tetroxide. Indications that fixation was inadequate can include disassociation of tissue structures, bubbles in tissue sections, poor and irregular staining, shrunken cells, clumping of cytoplasm, condensation and less distinct nuclear chromatin, and autolysisihemolysis of erythrocytes. A failure to preserve the micro-anatomical structure of the cellular specimen may adversely impact the analysis and lead to the potential for misdiagnosis.

Dehydration removes water from the tissue specimen to promote hardening. Specifically, the water molecules that reside in the space between the membranes of the cells making up the specimen are evacuated and replaced with molecules of the dehydrating agent. Replacement of this water in the tissue specimen with a dehydrating agent also facilitates subsequent replacement of the dehydrating agent with the solidifying material used in impregnation. This solution exchange is enhanced by using a volatile solvent for dehydration. The dehydrating agent may be low molecular weight alcohols, ketones, dioxane, alkylene glycols, or polyethylene glycols. Failure to dehydrate the specimen can lead to inadequate impregnation, poor ribbon formation during sectioning, clefts in tissue sections, dissociation of structures, water crystals in tissue sections, and poor staining.

Clearing is a process that enhances the ability to visualize the internal characteristics of cellular structure. The clearing step includes extracting dehydrating agent from the tissue specimen to reduce the tissue's opacity. Examples of clearants have traditionally included xylene, limonene, benzene, toluene, chloroform, petroleum ether, carbon bisulfide, carbon tetrachloride, dioxane, clove oil, or cedar oil.

Defatting of the tissue routinely occurs during the clearing operation, and is the process of removing fat (lipids) from the tissue specimen. If left in place, the fatty molecules would impair clearing and impregnation. Specifically, inadequate fat removal can result in spreading artifacts of tissue sections, wrinkling of tissue sections, and poor staining.

Once the tissue specimen is suitably fixed, dehydrated, and cleared, it is hardened by impregnation with a support medium such as wax, celloidin, polyalkylene glycols, polyvinyl alcohols, agar, gelatin, nitrocelluloses, methacrylate resins, epoxy resins, or other plastics. This step involves migration of the hardening agent into tissue cavities and cells that make up the tissue specimen. Appropriate hardening of the tissue specimen with adequate preservation of cellular morphology is required prior to placing the impregnated specimen in a block and obtaining thin sections. Preferred impregnation materials are commercial wax formulae, mixtures of waxes of different melting points (e.g., liquid mineral oil and solid paraffin), paraplast, bioloid, embedol, plastics and the like. Paraffin is often preferred because it is inexpensive, easy to handle, and ribbon sectioning is facilitated by the coherence of structures provided by this material.

It has long been a goal to decrease tissue processing times, thus allowing quicker analysis and diagnosis of the tissue sample. This is particularly important when tissue analysis is required as a part of a surgical procedure. However, in decreasing tissue processing times, the integrity of the tissue sample must remain high to facilitate accurate diagnosis. Many of the attempts to reduce the time of tissue processing have included the addition of heat energy during the processing steps so as to speed up the migration of process solution throughout the specimen and to facilitate chemical reactions occurring within the respective steps. For example, U.S. Pat. Nos. 4,656,047, 4,839,194, and 5,244,787 disclose the use of microwave energy; U.S. Pat. Nos. 3,961,097 and 5,089,288 disclose the use of ultrasonic energy; and U.S. Pat. No. 5,023,187 discloses the use of infrared energy.

Many of these prior art methods are undesirable for a number of reasons. One reason is that cellular structures, especially DNA and RNA, degrade when exposed to heat for prolonged periods of time. Such degradation makes analysis and diagnosis difficult or even impossible, and increases the risks of a misdiagnosis.

Prior art tissue processing methods can be broken into two main groups: conventional processing and microwave heat processing. Conventional processing methods employ vacuum and pressure with the chemical processing steps discussed above. Conventional methods may or may not include the addition of heat energy; however, any heat used is not produced by microwave energy. Microwave processing methods employ heat, vacuum, and pressure wherein the heat is produced by microwave energy.

The problem with conventional (non-microwave) methods is three fold. First, conventional methods have traditionally used hazardous chemicals that are known carcinogens to effectuate the chemical reactions during processing. Second, all tissue types are lumped together during tissue processing so that both "bound water" and "free water" molecules are removed from the tissue sample during processing, which damages the tissue sample. The ultimate goal of processing is to infiltrate the specimen with a hardening agent that is not miscible with the fresh or fixed specimen. Tissue samples are filled with free water that simply occupies the spaces among the biological molecules of carbohydrates, proteins, lipids and other compounds. This free water must be removed if the hardening agent is to enter.

There is a second type of water molecule in tissue specimen. This is referred to as bound water. Bound water is found surrounding nearly all macromolecules, being held to their surfaces by weak hydrogen bonds. It is not free to move around inside the tissue. It is not necessary to remove bound water in order to infiltrate the specimen with a hardening agent. Removal of bound water causes excessive hardening and shrinkage of the tissue sample. Also, bound water acts as a spacer among adjacent macromolecules, keeping them from coming close enough together to form hydrogen bonds between themselves. Once this insulating layer of bound water is removed, the tissue shrinks as macromolecules concentrate, and the specimen changes its cutting consistency as these molecules bind together. Fibrous tissue becomes tough and specimens comprised mostly of cells become crumbly. In conventional tissue processing, in the removal of free water from the larger, dense segments of the tissue specimen, bound water is also inadvertently removed from smaller, less dense segments, thus degrading those segments of the specimen. Third, for conventional processing methods processing times are usually in excess of 10 hours which means patients often have to wait until the following day for the tissue processing, analysis, and diagnosis. This relatively long time period can be detrimental and even life threatening for patients in situations where tissue analysis is urgently required. Because of this extended length of time, conventional tissue processing techniques may not be used for surgical analysis.

One problem with prior art microwave methods is that the heating of the tissue sample lacks uniformity. As is known in microwave technology, microwave energy produces hot spots and cold spots within the material being heated (target material). See Leong, Anthony S-Y, *Microwave Technology for Morphological Analysis*, Cell Vision, Vol. 1, No. 4 (1994). With only moderate success, attempts to reduce the occurrence of hot spots and cold spots have included fans inside the microwave chamber comprised of special material to disseminate the microwave energy, and rotating platforms to try to provide the target material uniform exposure to the microwave energy. The temperature within the hot spots can cause tissue destruction. Within the cold spots, the temperature may be inadequate to trigger or to complete the required chemical reactions. The result of the hot and cold spots is a lack of consistent processing of all of the cellular tissue comprising the specimen. Such a lack of consistency may result in poor or improper staining or analysis. The resulting potential for misdiagnosis may be dangerous and even life threatening for patients.

Another problem with microwave methods is that microwave energy may affect the bound water that physically separates macromolecules. Microwave energy is converted to kinetic and chemical energy. The kinetic energy results from the rapid oscillation of dipolar molecules causing internal heat. Although microwaves cannot ionize molecules and are too small to break molecular bonds, use of excessive microwave energy can redistribute the hydrogen bonds (chemical energy). Excessive microwave exposure also causes thinning of the bound water layers. This allows bound water layers to unwind and form new crosslinks, resulting in the formation of different configurations with a resultant potential for misdiagnosis.

Another problem with microwave energy in tissue processing is that microwave energy is only capable of penetrating the tissue to only a limited depth. See Kok L P, Visser P E, *Histoprocessing with the Microwave Oven: An Update*, Histochem J. 1988 June-July; 20 (6-7): 323-8. This means that in order to effectively use microwave energy for tissue processing, the tissue samples must be very thin. Thin samples are more difficult to handle and they can also be more difficult to obtain. If the sample is not sufficiently thin, then the cells comprising the outer portion of the tissue sample may process differently than the cells comprising the inner portion of the tissue sample. Attempts to overcome this limitation by increasing the amount of microwave energy to penetrate more deeply into the sample can damage the cell structure, DNA, and RNA, as discussed above.

Yet another problem with microwave energy in tissue processing is that microwave energy only affects molecules with an electric dipole. Molecules with an electric dipole are known as polar, while those with little or no electric dipole are known as nonpolar. Water is a polar molecule. A water molecule has a positive charge at one end and a negative charge at the other, and is therefore twisted to and fro as it tries to align itself with the alternating electric field induced by microwaves. This molecular movement creates heat. The different concentrations of free and bound water within the specimen means that some water molecules in the tissue will be heated more than other water molecules in the tissue, thus contributing to the inconsistent heating. Microwave heating is more efficient on liquid unbound water, and much less so on fats, sugars and the like. Microwave tissue processing involves a series of events in which a tissue specimen is sequentially processed through various chemicals ranging from polar to nonpolar. As dehydration occurs and free water is removed, bound water is left behind. This bound water is a highly polarized molecule, and, therefore, is the most affected by microwave energy. Over heating of this bound water can lead to tissue distortion causing a "cooked" tissue sample. This potential for tissue distortion after dehydration is exacerbated by the fact that most traditional processing chemicals are nonpolar. Thus, excessive microwave energy is required to build up enough heat to bring about the desired chemical reactions. To minimize tissue distortion there should be a gradual change in polarity of the processing solutions from highly polar aqueous fixatives to nonpolar hardening agents.

In addition to the above referenced problems that have been encountered using microwave energy in tissue processing, there have also been attempts to use more environmentally friendly and user friendly solvents in tissue processing. Traditional solvents used in tissue processing include xylene, limonene, benzene, toluene, chloroform, and petroleum ether. These solvents are harsh in that they can damage the tissue sample. These traditional solvents are generally capable of over-hardening and shrinking tissue. Increasing the exposure to these solvents may help the processing of fatty tissue but only at the expense of delicate small biopsies.

Tissue porosity has a major impact on processing. Porosity at an ultrastructural level is determined by the nature of the tissue and the effects of processing reagents to which the tissue are subjected. Tissue porosity is a function of the number and size of natural and artificial pores, and the swelling and shrinkage of the biopolymer matrix. Even after fixation, cell surfaces continue to act as osmotic membranes. Regardless of fixative process solution used, all tissue undergoes limited shrinkage and hardening during dehydration, clearing and infiltration. Hardening generally results from tissue shrinkage, accompanied in most cases by decreased porosity. Fatty tissue specimens usually require extended processing as lipids inhibit the diffusion of processing solution. This extended processing requirement has a tendency to decrease porosity, inhibiting the removal of lipids.

These traditional solvents also present a risk to the laboratory personnel. Further, they require careful disposal so as to not damage the environment. For all of the above reasons, it would be desirable to use solvents that are not so harsh to the tissue sample, to the user, or to the environment.

It is therefore an object of the present invention to provide a rapid, efficient, and high quality tissue processing method.

It is further an object of the present invention to provide a tissue processing method that employs the benefits of ohmic heating.

It is further an object of the invention to use chemicals that provide superior processing attributes, are safer to handle, and are more environmentally friendly than current chemicals being used in tissue processing.

SUMMARY OF THE INVENTION

The present invention is a method for the rapid processing of a tissue sample. The process includes the four general steps of fixation, dehydration, clearing, and impregnation (infiltration). In the preferred embodiment, more than one of the steps can be performed simultaneously using a single solution. After collecting the tissue sample, the first step of the processing method is to enclose the tissue sample in a cassette which is then placed in a cassette rack, as is known in the art. The rack is placed in a processing container with conductive leads on the container walls. The container is placed in the processing unit and connected to the electrical power source. The rack is oriented in such a manner as to expose the openings in the cassettes with the flow of electrical current between the conductive leads. The container is filled with the proper processing solution or material into which is added a conductive agent to facilitate the resistive flow of electricity through the tissue specimen. It has been determined that a conductive polymer acts as the best conductive agent. During the fixation, dehydration, clearing, and impregnation steps, the present invention uses a combination of ohmic and microwave energy to heat the sample to achieve rapid tissue processing and thereby reduce the time the tissue is exposed to heat.

The use of microwave energy is known in the tissue processing field. Ohmic heating is achieved by introducing an electric current from a power source to the conductive leads on the processing container. It flows across the processing solution containing the conductive agent. The solution and the tissue specimen each provide resistance to the flow of electricity which results in conversion of electric current to heat energy. The electric current also facilitates chemical exchange by causing molecular oscillation of the processing solution while inhibiting protein migration in the tissue sample. A temperature probe is used to monitor the temperature of the solution. During the tissue processing steps, the invention alternates between microwave energy and ohmic energy to bring the processing solution and tissue specimen to the desired temperature, and to maintain the solution and specimen at the desired temperature for the required period of time. In the preferred embodiment, the processing unit has a chamber combined with a vacuum means and a means for introducing the various solutions and reagents into the processing container without having to manually add and remove different processing solutions from the processing container.

There are currently three preferred embodiments of the invention:

1. The "Short Run" takes about 10 to 15 minutes, a first step comprising a first solution effectuates fixation, dehydration, and clearing, and a second step which effectuates infiltration occurs in a second solution.

2. The "Intermediate Run" takes about 1 hour, a first step comprising a first solution effectuates fixation and some dehydration, a second step comprising a second solution effectuates more dehydration and some clearing, a third step comprising a third solution effectuates more clearing and some infiltration, and a fourth step comprising a fourth solution completes infiltration.

The "Long Run" takes about 2 hours, a first step comprising a first solution effectuates fixation and some dehydration, a second step comprising a second solution effectuates more dehydration and some clearing, a third step comprising a third solution effectuates more clearing, and a fourth step comprising a fourth solution that effectuates more clearing and some infiltration, and a fifth step comprising a fifth solution that completes infiltration.

DESCRIPTION OF THE PREFERRED EMBODIMENT OF THE INVENTION

Figure 1:
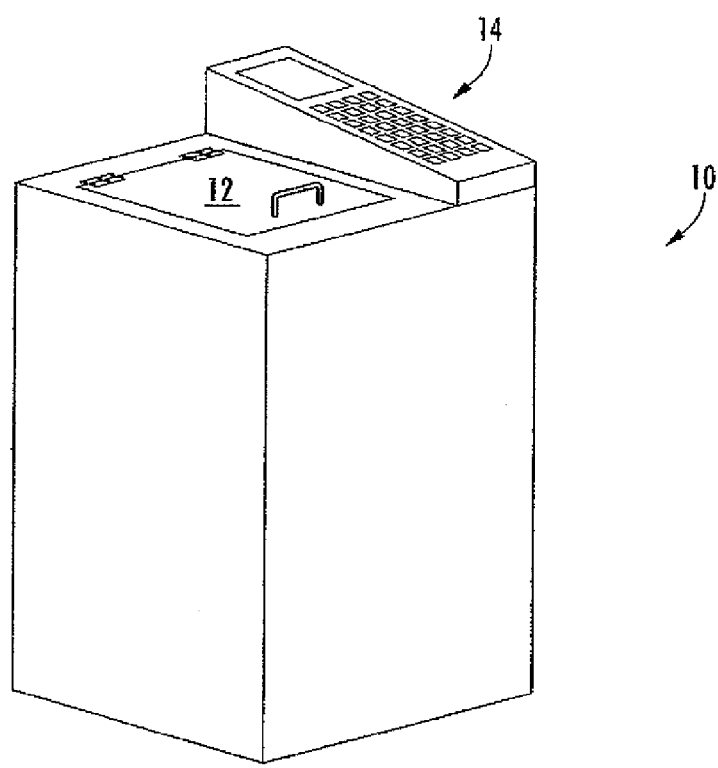
FIG. 1 is a perspective view of the tissue processor of the present invention.

The present invention is a method for the rapid processing of a tissue sample. The steps of fixation, dehydration, clearing, and impregnation (sometimes herein referred to as infiltration) can be rapidly performed in a period of time ranging from about ten minutes to about two hours, based on the tissue type and size, and, further, depending on the selected processing protocol. FIG. 1 shows the tissue processing unit 10 having a control panel 14 and a loading door 12. The processing unit 10 can be of any size and shape so long as it contains all relevant components to process the tissue sample. The loading door 12 can be of any type so long as it provides access to the processing chamber 13. The control panel 14 comprises various controls for adjusting the temperature, run time, run cycle, and the like. Preferably, the control panel 14 also comprises a screen for displaying a variety of information, such as the temperature of processing solution inside the chamber 13 and the time and steps remaining in the run cycle.

Figure 2:
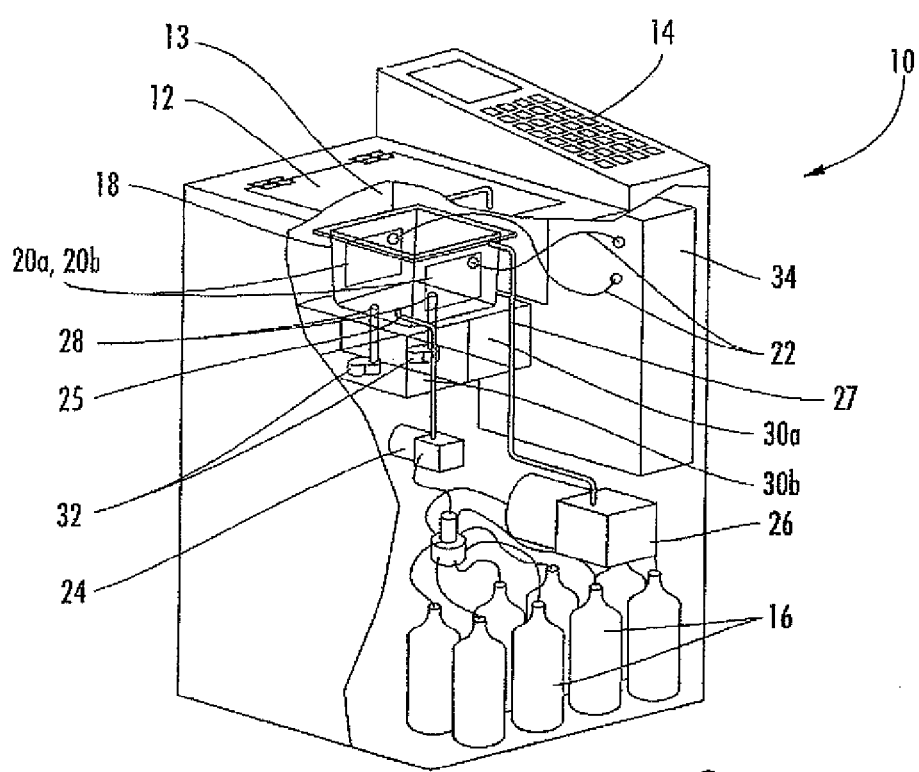
FIG. 2 is a perspective view of the tissue processor of the present invention with the exterior portion cut away so as to show the internal components.
Figure 3:
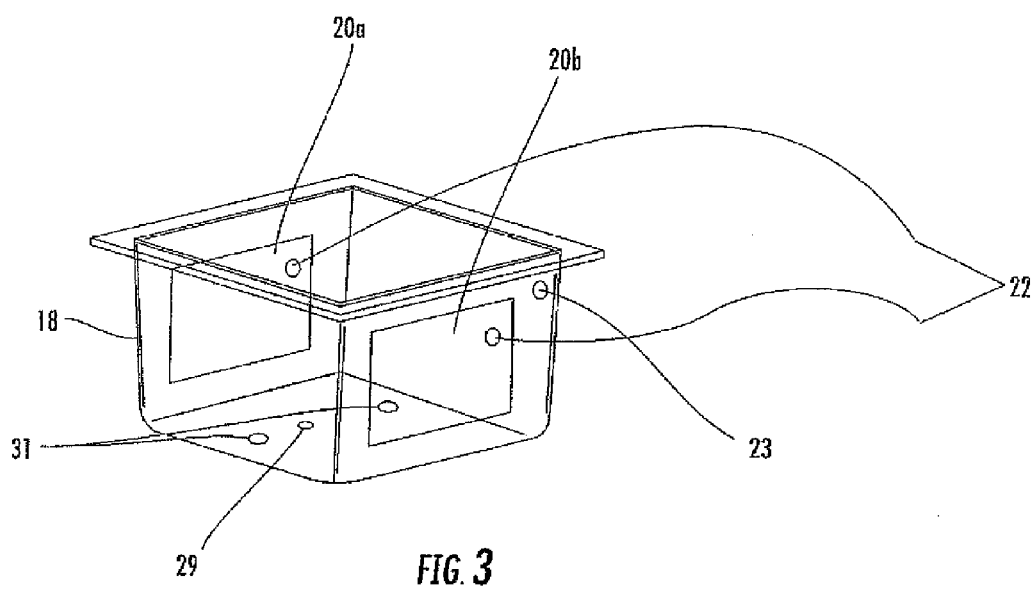
FIG. 3 is a perspective view of the processing container.

FIG. 2 shows the processing unit 10 with a portion of its exterior wall cut away so as to expose the interior components. The loading door 12 opens into the processing chamber 13. The processing chamber 13 is large enough to accommodate the processing container 18, which is best seen in FIG. 3. Lead wires 22 combine a power source 34 to the electrodes 20, which are embedded within the interior side walls of the processing container 18. In the automated embodiment, there is at least one infiltration reservoir 30a below the processing chamber 13. In the preferred embodiment, there are two reservoirs 30a, 30b, each containing a different infiltration solution for different processes. The infiltration reservoirs 30a, 30b are containers for storing infiltration solutions such as paraffin wax, and heating it so it remains in a molten state. During the infiltration step, or any other step requiring an infiltration solution, the infiltration solution stored in the reservoirs 30a, 30b is introduced into the processing container 18 by pumps 32, which pump the solution through connection means 28a, 28b respectively, and into the processing container 18. There are ports 31 in the processing container 18 adapted to receive the connection means 28a, 28b. When the infiltration step is competed, the pumps 32 remove the solution from the processing container 18, through the connection means 28a, 28b, and back into the reservoirs 30a, 30b so that the solution may be reused in the processing of a subsequent tissue sample.

As seen in FIG. 2, reagent bottles 16 are stored in or near the processing unit 10. Examples of the processing fluids stored in these bottles and used to effectuate the chemistry in the processing steps are illustrated in Tables 1 and 2 below. In the preferred embodiment, a reagent pump 24 is adapted to introduce and remove reagents to and from the processing container 18 through a reagent connection tube 25 which combines with the processing container 18 through reagent ports 29. After being removed from the processing container 18, the reagents may be reused in processing a subsequent tissue sample. Also shown in FIG. 2 is a vacuum pump 26 which is in communication with the processing chamber 13, preferably through a vacuum tube 27. The vacuum tube 27 is combined with the processing container 18 through a vacuum port 23 adapted to receive the vacuum tube 27. The vacuum pump 26, when activated, operates to lower the atmospheric pressure within the processing chamber 13. The lower atmospheric pressure functions to remove air from the tissue cassettes and to de-gas the processing fluids. The removal of gas from the cassettes and the processing fluids is particularly beneficial to infiltration.

As noted above, the present invention allows the reuse of processing fluids which allows a reduction in the total amount of processing fluids used over a period of time. In tests recently performed by Applicant, conventional tissue processing consumed about seventeen gallons of processing fluids per week, whereas the present invention consumed approximately five gallons of processing fluids for the same period of time.

The present invention comprises the afore mentioned steps of fixation, dehydration, clearing, and impregnation. Fixation, dehydration, and clearing are required for the preparation of tissue prior to impregnation. These steps are facilitated by trimming the tissue to a suitable size prior to processing, and using cassettes which hold such tissue blocks in place for fixation, dehydration, removing fat, and impregnation. Each step is effectuated by the introduction of a chemical solution into the processing chamber 18. As is further describe below, each chemical solution is mixed with a conductive agent to allow the controlled flow and resistance of electricity across the solution and the specimen. In certain embodiments, there are more than one dehydration, clearing, and infiltration steps to allow for more complete tissue processing.

Fixation initiates hardening of the tissue specimen, and further preserves cell morphology by cross linking proteins and halting cellular degradation. Preferably, due to the significant amount of water contained within the tissue, the present invention uses somewhat aqueous solutions during the fixation process. Use of a totally non-aqueous solution at this stage could "shock" or rapidly dehydrate the tissue thereby damaging the tissue sample. After the fixation step, most processing fluids are non-aqueous. Examples of fixative agents are listed below in Tables 1 and 2.

Dehydration removes unbound water from the intercellular areas of the tissue specimen. This promotes hardening. Replacement of water in the tissue specimen with a dehydrating agent also facilitates subsequent replacement of the dehydrating agent with material used for impregnation. As discussed above, the tissue sample contains water that is both bound and free. Bound water is that which is inside the cells. Removal of bound water would severely damage the cellular structure and render the specimen unsuitable for further testing or diagnostic analysis. In an alternate embodiment, the invention utilizes a super-absorbent, water-soluble polymer (such as polyacrylate) to absorb water on contact. As the tissue undergoes dehydration, the processing solution traps and carries away the free water molecules. If the solution is thereafter filtered through a system as described above, this will remove the water molecules allowing for the continued reuse of the processing solution. Examples of dehydrating agents are listed below in Tables 1 and 2.

Clearing is the process of removing the dehydrating agent and fats. This increases the tissue sample opacity. Defatting dissolves lipid molecules in the tissue. The process of defatting is not so harsh that it breaks down the cell membranes. Examples of clearing agents are listed below in Tables 1 and 2.

Infiltration is the process of hardening the tissue sample by filling the area previously occupied by free water and fatty molecules with a wax substance such as paraffin wax or soy wax. Appropriate hardening of the tissue specimen with adequate preservation of cellular morphology is required prior to cutting thin tissue samples for analysis. After the paraffin hardens, the tissue is easier to handle, stain, and slice. Examples of infiltration agents are listed below in Tables 1 and 2.

Embedding is an optional step that can be employed after the above described tissue processing steps are completed. Embedding is the process of taking the impregnated tissue and encasing it in an additional paraffin layer. This additional paraffin layer makes the encased tissue sample easier to handle because the additional paraffin simply provides a larger area with which to handle the tissue sample.

Examples of the processing solutions that can be used to carry out the above identified steps are listed below in Tables 1 and 2. It should be noted that Tables 1 and 2 do not represent a comprehensive list of chemicals and solutions that can be used in the present invention.

TABLE 1

Solutions and Reagents:

CLEARING AGENTS:

V.M. & P. Naptha;
Light aliphatic solvent naptha;
Heavy hydrotreated naptha;
Octanes;
Nonanes;
d-limonene;
aliphatic hydrocarbons;
synthetic fatty alcohols;
naptha isoparaffinic - hydrocarbons;
Fatty acid methyl esters;
Vegetable oils;
Castor oil;

SOLVENTS:

Ethyl hydroxy propionate (Ethyl Lactate);
synthetic fatty alcohols;
natural fatty alcohols;
propyl acetate;

TABLE 1-continued

Solutions and Reagents:

ethyl acetate;
ethyl alcohol;
dimethyl sulfoxide;
ethyl 3-hydroxybutyrate (EHB) methyl or butyl 3-hydroxybutyrate;
Propylene Carbonate;

INFILTRATION AGENTS:

soy wax;
paraffin wax;
polymers;
plastic;

CONDUCTIVE AGENTS:

Liquid electrolytes;
Conduction polymers - polyanilines, polypyrroles,
polythiophenes & thiophene oligomers, polyphenylene
sulfides;
Carbon;
Metal nanoparticles;
Ionic liquids - halogen-free ionic liquids,
imidazolium derivatives, pyridinium derivatives;

SURFACTANTS:

polyethylene glycol - 300 molecular weight;
fatty acid based surfactants polyhydroxyl
surfactants.

The preferred embodiment of the invention employs all "green chemicals." Green chemistry is defined as the invention, design, and application of chemical products and processes to reduce or eliminate the use and generation of hazardous substances. Examples of green chemicals are chemicals produced from alternative biomass feedstocks rather than petroleum, such as fatty acid methyl esters, ethyl lactate, soy wax, non-halogenated ionic liquids, fatty acid based surfactants and the like. Other examples of green chemicals that can be used in the invention are listed in Table 2.

Although the preferred embodiment employs all green chemicals, the present invention can also be carried out using all traditional processing solutions, which are primarily derived from petroleum, or the present invention may use a mixture of green chemicals and petroleum chemicals. A significant advantage to using green chemicals is that they are less harsh on the tissue sample than traditional solvents such as xylene, limonene, benzene, toluene, chloroform, and petroleum ether. Green chemicals have a broader polarity range than conventional chemicals lending to increased tissue porosity. Those with lower molecular weights diffuse through tissue more quickly than traditional solvents. These green chemicals provide a better processed tissue sample, they are safer to handle, and they are less damaging to the environment.

TABLE 2

Green Chemicals:

CLEARING AGENTS:

d-limonene;
synthetic fatty alcohols;
fatty acid methyl esters;
vegetable oils;
castor oil;

SOLVENTS:

Ethyl hydroxyl propionate (Ethyl Lactate);
Synthetic fatty alcohols;

TABLE 2-continued

Green Chemicals:

Natural fatty alcohols;
Propyl acetate;
Ethyl acetate;
Ethyl alcohol;
Ethyl 3-hydroxybutyrate (EHB);
Methyl or butyl 3-hydroxybutyrate;
Propylene carbonate;

INFILTRATION AGENTS:

Soy wax;
Biopolymers;

CONDUCTIVE AGENTS:

Conducting polymers;
Polyaniline;
Polypyrroles;
Polythiophenes;
Thiophene oligomers;
Polyphenylene sulfides;
Ionic liquids;
Halogen free ionic liquids;
Imidazolium derivatives;
Pyridinium derivatives;
Carbon;
Metal nanoparticles;

SURFACTANTS:

Fatty acid based surfactants;
Polyhydroxyl surfactant;

In the preferred embodiment, the above referenced steps of fixation, dehydration, clearing, and infiltration are not independent steps with independent processing solutions. In some embodiments, more than one step is performed at the same time using a single solution. In other embodiments, some of the steps may be performed more than once using different solutions to achieve the most effective tissue processing. The concentrations of the different solutions used to effectuate each step can vary widely depending on the specific type of chemical used and the purpose of the processing, i.e. the analysis to be performed after the processing. Specific examples of solutions and concentrations are defined below in the Short Run, Intermediate Run, and Long Run preferred embodiments. For example, in the "Short Run" embodiment described below, fixation, dehydration, and clearing are all performed in a single step using only one solution. When only one solution is used to carry out more than one step, the solution is comprised of several of the conventional reagents of Table 1 and/or green chemicals of Table 2. Since only one solution is used to perform several steps, processing time is shortened because only one solution needs to be heated instead of two solutions. Similarly, dehydration and clearing can be performed simultaneously in the same step. For example, a mixture such as ethanol and ethyl lactate, or ethanol and aliphatic hydrocarbons can be used to effectuate dehydration and clearing at the same time. The ethyl lactate and ethanol mixture can be used in the green chemical embodiment, and the ethanol and aliphatic hydrocarbon mixture can be used in the conventional chemistry embodiment.

Figure 4:
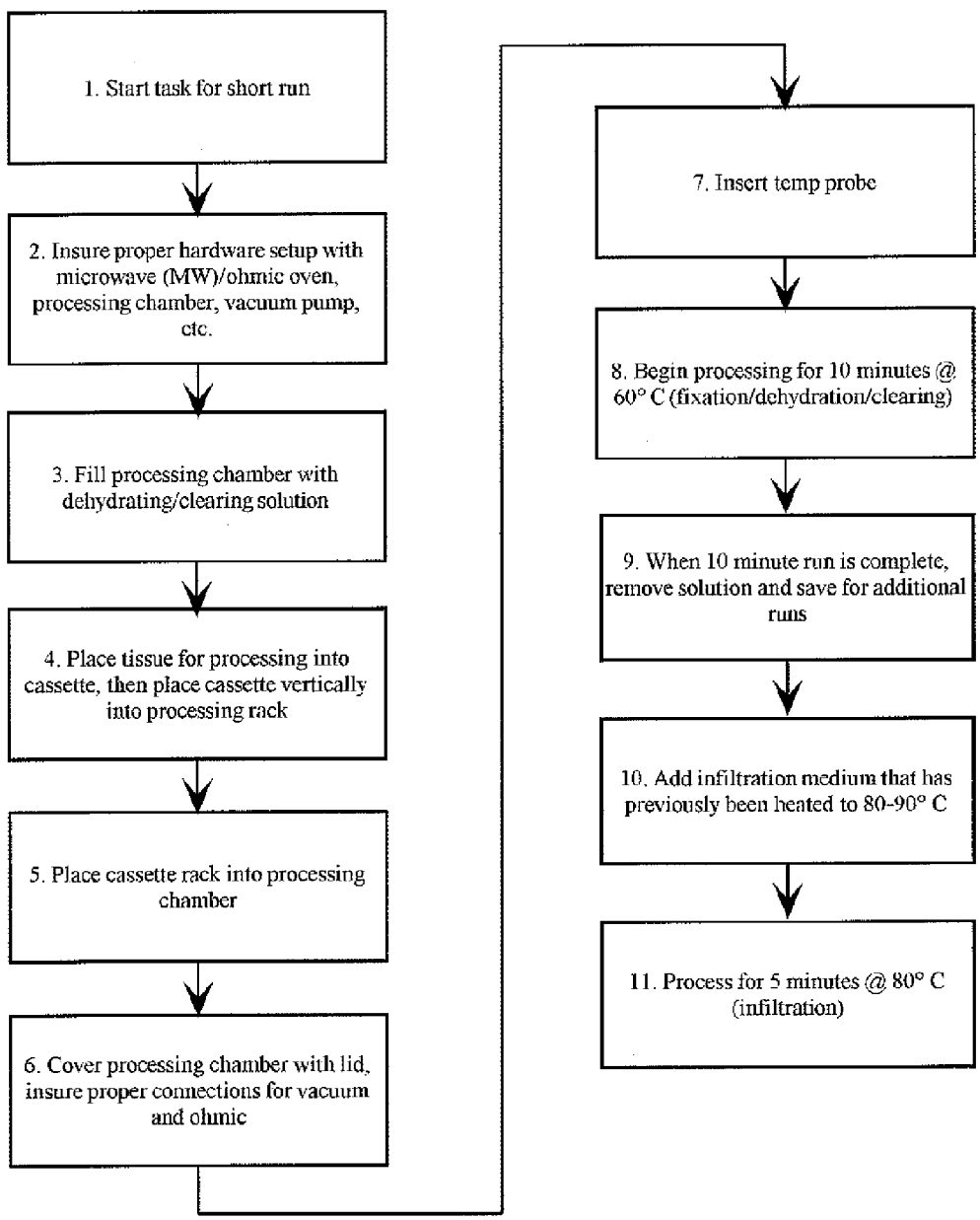
FIG. 4 is a flow chart of the "short run" embodiment.
Figure 5:
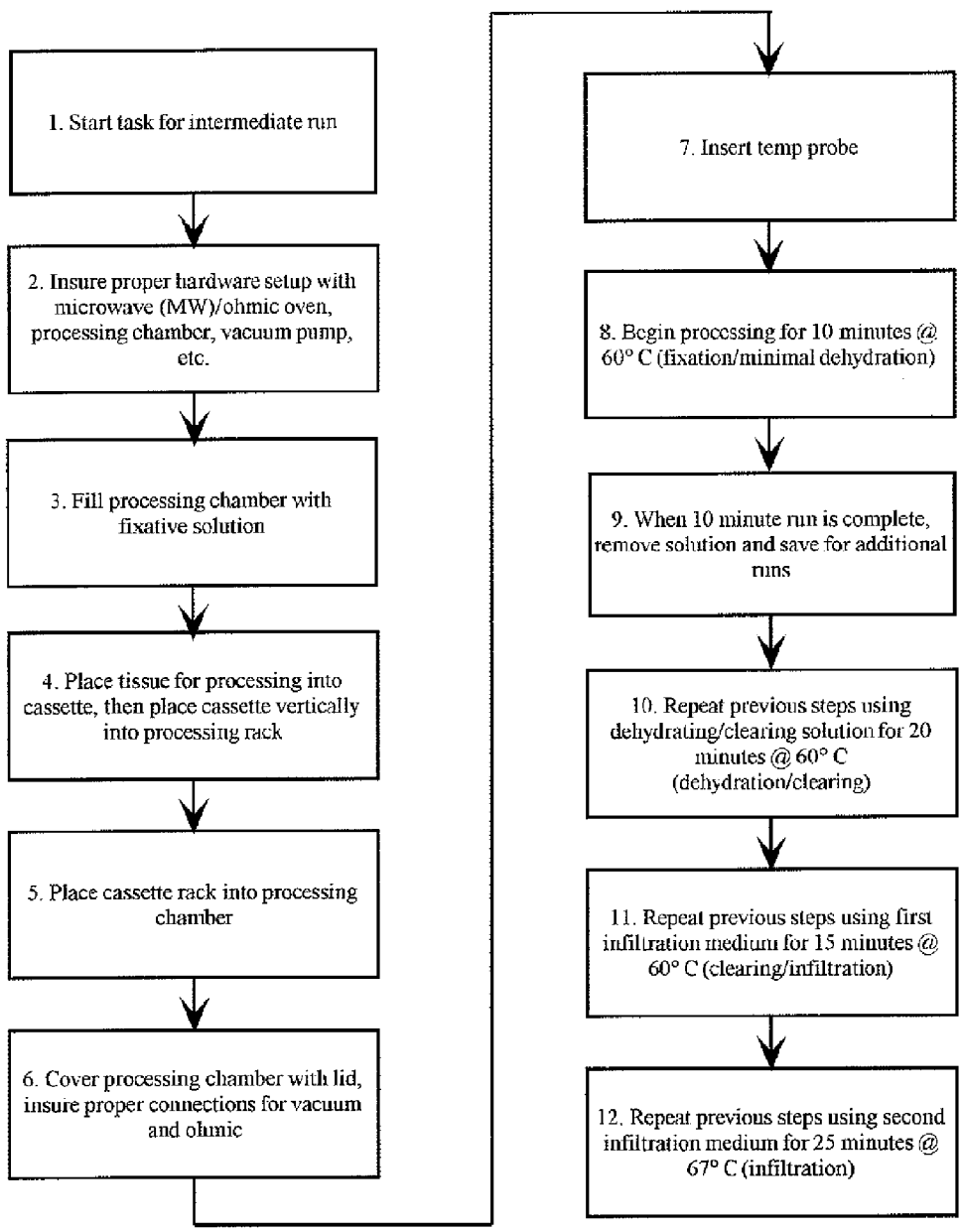
FIG. 5 is a flow chart of the "intermediate run" embodiment.
Figure 6:
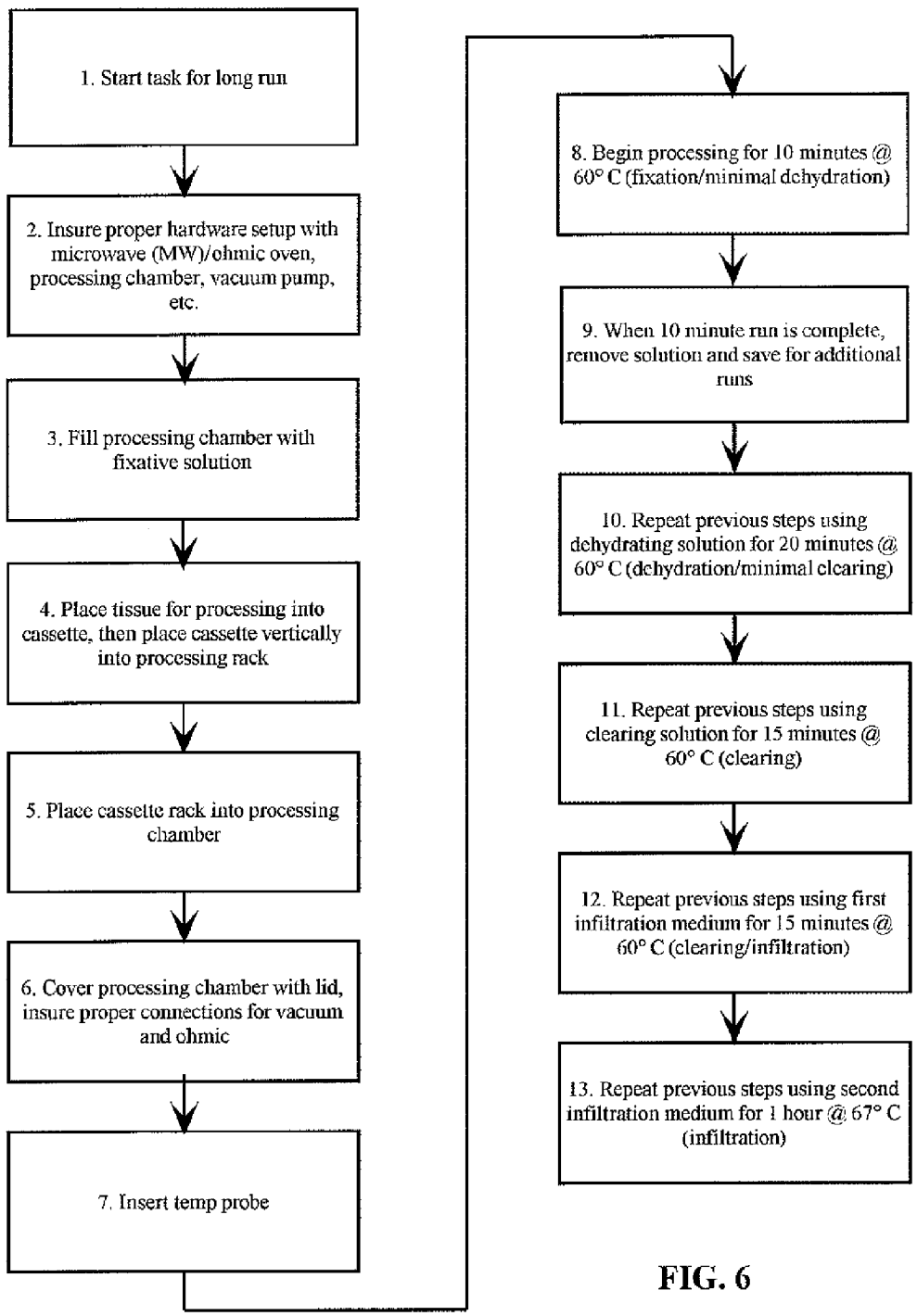
FIG. 6 is a flow chart of the "long run" embodiment.

FIGS. 4, 5, and 6 are flow charts that outline the three preferred methods for carrying out the present invention. The preferred voltage, resistance, amp, and frequency ranges for the preferred embodiments are set fourth below following the three preferred embodiments.

FIG. 4 shows the "Short Run" embodiment comprising the steps of:

1. insure proper hardware setup with the processing unit, processing chamber, vacuum pump, solutions, etc.;

2. fill the processing chamber with the first solution which comprises between 33.3-66.6% dehydrating agent and 33.3-66.6% clearing agent, and 0-10% conductive agent;

3. place tissue for processing into cassette, then place cassette into processing rack;

4. place the cassette rack into processing chamber so that the tissue is submerged in the dehydrating/clearing solution mixture;

5. cover processing chamber with lid to ensure a seal for the vacuum, insure proper connections for vacuum and ohmic;

6. insert temperature measuring means;

7. process in the solution for about 10 minutes at 60 C using alternating cycles of ohmic and microwave energy to achieve and maintain the temperature, this processing step fixes, dehydrates, and clears the tissue sample;

8. when 10 minutes run is completed, remove solution and save for subsequent processing;

9. add between 75-100% infiltration medium, and 0-15% conductive agent that has previously been heated to 80-90 C; and 10. process for 5 minutes in infiltration medium at 80 C using alternating cycles of ohmic and microwave energy to achieve and maintain the temperature, this processing step infiltrates the tissue sample.

FIG. 5 shows the steps for the "Intermediate Run"

1. insure proper hardware setup with processing unit, processing chamber, vacuum pump, solutions, etc.;

2. fill processing chamber with a solution which comprises between 75-100% fixative, 0-25% dehydrating agent, 0-25% surfactant, and 0-25% conducting agent;

3. place tissue for processing into cassette, then place cassette into processing rack;

4. place cassette rack into processing chamber so that tissue sample is submerged in the fixative solution;

5. cover processing chamber with lid, insure proper connections for vacuum and ohmic;

6. insert temp measuring means;

7. process in the solution for 10 minutes at 60 C using alternating cycles of ohmic and microwave energy to achieve and maintain the temperature, this processing step fixes and minimally dehydrates the tissue sample, the heat is maintained by alternating cycles of microwave and ohmic energy;

8. when 10 minutes run is completed, remove solution and save for subsequent processing;

9. repeating previous steps using between 50-100% dehydrating agent, 50-100% clearing agent, 0-10% surfactant, and 0-10% conducting agent for 20 minutes at 60 C using alternating cycles of ohmic and microwave energy to achieve and maintain the temperature, this processing step continues dehydrating and begins clearing the tissue sample;

10. repeating previous steps using first infiltration medium which comprises between 50-75% clearing agent, 25-50% infiltration agent, 0-10% conductive agent, and 0-10% surfactant for 15 minutes at 60 C using alternating cycles of ohmic and microwave energy to achieve and maintain the temperature, this processing step continues clearing and begins infiltrating the tissue sample; and 11. repeating previous steps using second infiltration medium comprising between 75-100% infiltration agent, 0-25% clearing agent, 0-10% surfactant, and 0-10% conductive agent for 25 minutes at 67 C using alternating cycles of ohmic and microwave energy to achieve and maintain the temperature, this processing step completes infiltrating the tissue sample.

FIG. 6 shows the steps for the "Long Run"

1. insure proper hardware setup with processing unit, processing chamber, vacuum pump, solutions etc.;

2. fill processing chamber with fixative solution comprising between 75-100% fixative, 0-25% dehydrating agent, 0-10% surfactant, and 0-10% conducting agent;

3. place tissue for processing into cassette, then place cassette into processing rack;

4. place cassette rack into processing chamber so that tissue sample is submerged in the fixative solution;

5. cover processing chamber with lid, insure proper connections for vacuum and ohmic;

6. inserting temp measuring means;

7. process in the fixative solution for 10 minutes at 60 C using alternating cycles of ohmic and microwave energy to achieve and maintain the temperature, this processing step fixes and minimally dehydrates the tissue sample;

8. when 10 minutes run is completed, remove solution and save for subsequent processing;

9. repeating previous steps using dehydrating solution comprising between 50-100% dehydrating agent, 50-100% clearing agent, 0-10% surfactant, and 0-10% conductive agent for 20 minutes at 60 C using alternating cycles of ohmic and microwave energy to achieve and maintain the temperature, this processing step completes dehydration and minimally clears the tissue sample;

10. repeating previous steps using clearing solution comprising between 50-75% clearing agent, 25-50% infiltration agent, 0-10% conductive agent, and 0-10% surfactant for 15 minutes at 60 C using alternating cycles of ohmic and microwave energy to achieve and maintain the temperature, this processing step continues clearing of the tissue sample;

11. repeating previous steps using first infiltration medium comprising between 75-100% infiltration agent, 0-25% clearing agent, 0-10% surfactant, and 0-10% conductive agent for 15 minutes at 60 C using alternating cycles of ohmic and microwave energy to achieve and maintain the temperature, this processing step continues clearing and begins infiltrating the tissue sample; and 12. repeating previous steps using second infiltration medium comprising between 75-100% infiltration agent, 0-25% clearing agent, 0-10% surfactant, and 0-10% conductive agent for 1 hour at 67 C using alternating cycles of ohmic and microwave energy to achieve and maintain the temperature, this processing step completes infiltrating the tissue sample.

The prior art has employed a number of different sources of heat energy for use in tissue processing, including microwave, infrared radiation, and ultrasonic. Ohmic heat has not been employed in the past because conventional organic chemicals used in tissue processing do not conduct electricity. In order to overcome this inability, the present invention uses conducting polymers. Conducting polymers, such as Polyaniline, produced by Panipol Company in Finland, are unique in that they conduct electricity, yet they do not interfere with the binding sites of the tissue molecules. Traditional non-conductive tissue processing chemicals require the addition of salt in order to allow the chemicals to be conductive. The salt interferes with the binding sites of the tissues and thus produces poor processed tissue samples.

The main purpose of applying heat to the processing solutions and tissue during tissue processing is to increase the migration of the processing solution throughout the specimen and to speed up the chemical reactions occurring in the processing. The present invention uses a combination of microwave and ohmic heat to bring the processing solution and tissue sample up to, and to maintain the processing solution and tissue sample at the most advantageous temperature for facilitation of the desired reactions. Without regard to potential damage to the specimen by prolonged exposure, microwave energy has been found to be a faster source of energy for bringing the processing solution up to desired temperature, and electrically created ohmic heat has been found to be a better source of energy for maintaining the processing solution at is desired temperature. In the preferred embodiment, the present invention alternates between the introduction of microwave and ohmic energies to bring the processing solution up to temperature and to maintain it at its optimum temperature. Although the frequency can vary, the preferred embodiment alternates between microwave and ohmic energy about once per second. When the solution reaches its target temperature, both ohmic and microwave heating stops until the solution falls below the target temperature, at which time the ohmic and microwave energies turn back on to warm the solution back up to its target temperature. It should be noted that ohmic heat alone can accomplish the process of the present invention; however, it has been found that ohmic heat in combination with microwave heat energy produces better results.

The power supply 34 provides the electrical lead wires 22 with electricity. The processing container 18 has two conductive electrodes 20. The electrical lead wires 22 combine the power supply 34 with the electrodes 20 on the processing container 18. The processing container 18 is filled with a processing solution and a conductive agent such as liquid electrolytes, conducting polymers, or ionic liquids. The processing container 18 is then placed into the processing unit 10. The conductive agent has at least some resistance to electricity, so that as electricity is introduced through the processing solution containing the conductive agent, the resistance of the conductive agent turns the electrical energy into heat energy. The amount of heat used to maximize tissue processing efficiency can vary depending on many factors, including the type of tissue being processed. The amount of heat energy can be changed by varying the amount of electrical energy provided to the electrodes 20, or by using different conductive agents or concentrations of conductive agents with differing resistance properties. The preferred conductive agent is a polymer called polyaniline. Polyaniline is used to control the amount of resistance in the sample. Polyaniline is a good conductor whereas the tissue sample is a poor conductor. Polyaniline can be used to increase the ease with which electricity passes through the solution and tissue sample, thus creating heat energy, while keeping the temperature within a range that will not destroy or burn the sample. Polyaniline is used in differing amounts to obtain the desired amount of conductivity/resistance/heat. The preferred concentrations of conductive agents such as Polyanine are disclosed above in the preferred embodiments of the Short Run, Intermediate Run, and Long Run.

The parameters used during tissue processing such as frequency of the alternating current, applied voltage, time of processing, and temperature to which the sample is heated all have a significant effect on the outcome of the sample. Each chemical or solution used in the particular processing run may have its own preferred ranges of volts, current, resistance, temperature, time, and frequency. Preferred ranges of solution concentrations, processing times, and processing temperatures are disclosed above in the three preferred embodiments. Although the preferred embodiments of these variables are disclosed herein, it should be noted that these variables may change slightly depending on the size of the tissue sample, age of the solutions, elevation, and other such factors. Preferred ranges for the variables relating to the microwave energy and ohmic energy used in the present invention are disclosed below.

The use of microwave energy in tissue processing is known. Microwaves operate in a frequency range lower than radio waves but longer than infrared, usually between one (1) and three-hundred (300) GHz. The preferred embodiments of the present invention use microwave energy at a frequency of about 2.4 GHz.

The amount of current and voltage passed through the solution to achieve the target temperature using ohmic heat will depend on the resistance of the solution being used. To determine the resistance of the solution, a conductivity meter should be used. Conductivity meters are known in the art. In the preferred embodiment, a conductivity meter is built into the processing unit 10 and is adapted to measure the conductivity of the processing solution using the lead wires 22 and the electrodes 20a, 20b on the processing container 18. The resultant conductivity can be displayed on the control panel 14.

The overall conductivity of the processing solution should be between 0.001 and 100 Siemens depending on the target temperature and solution being used for the particular processing run. Conductivity is the inverse of resistance, so once conductivity is measured with the conductivity meter, a value for resistance can be entered into Ohm's law. Ohm's law states I=V/R, where I is current in amps, V is voltage in volts, and R is resistance in Ohms. Power is the rate at which electrical potential energy is converted to other forms of energy such as thermal energy. Power is calculated by the formula P=IV, where P is power in watts, I is current in amps, and V is voltage in volts. If the resistance (R) is too high, the current (I) at maximum voltage (V) will be too low and therefore the power (P) will be too low to produce adequate thermal energy (heat). If resistance (R) is too low, the maximum current (I) will be reached at low voltage (V) and the power (P) will be too low to produce adequate thermal energy. The current (I) and the voltage (V) must be of a range to produce sufficient power (P) for adequate thermal energy (heat) to bring about the necessary chemical reactions. Preferred processing temperatures have been given in the three preferred embodiments above and those temperatures range from about 60 degrees C. to about 90 degrees C. If power (P) is too high, then the temperature will rise too rapidly. If power (P) is too low, rise in temperature will not occur or will occur too slowly. An example of the ohmic energy settings for a typical dehydration step comprising 50% dehydrating solution (such as ethanol), 23.5% ethyl lactate, 23.5% methyl ester, 3% polyaniline is to have the current set to 0.3-0.8 amps, and the voltage set to 300 volts.

Ohmic energy introduced in the present invention can use between thirty (30) and three-thousand (3000) Hz. In the preferred embodiments, about five-hundred (500) Hz is used. This number of cycles of energy may help improve molecular oscillation, which may facilitate complete diffusion of the processing solution throughout the specimen to maximize complete chemical reactions. Further, increased cycles of energy prevent proteins from migrating in the tissue specimen and prevent electrode degradation.

As discussed above, prolonged or excessive exposure to heat of any kind can initiate a process of degradation. One advantage of using ohmic heating in combination with microwave energy is that it allows for a shorter overall heating time. Variable tissue density affects infiltration and subsequent microtomy. Spongy, parenchymatous tissues are usually more rapidly infiltrated than hard, dense, fibrous tissues. Density also influences the rate of diffusion of the processing solution throughout the specimen, thus impairing processing time. The advantage of ohmic heating is that it uniformly heats tissues irrespective of the tissue density of the specimen. Therefore, the ability of the ohmic heat to shorten the time that the tissue is exposed to heat actually helps to preserve and maintain the tissue, DNA, and RNA. A second advantage of ohmic heating is that it produces even and consistent heating without sporadic hot or cold spots.

Another advantage provided by the use of an ohmic energy heat source is its ability to maintain a steady temperature throughout the tissue specimen. As discussed above, microwave energy is not uniform in that it produces hot spots and cold spots. The hot spots can degrade the tissue and the cold spots can produce poor or non-completed chemical reactions. The hot and cold spots can cause different portions of the same tissue sample to yield different cellular appearance. This can lead to improper diagnosis which is dangerous for patients. In contrast, microwave energy combined with ohmic heat provides a uniform temperature throughout the processing solution and submerged tissue sample which allows for more uniform results and a more accurate, consistent diagnosis.

In the preferred embodiment, the present invention is carried out in a processing unit 10 that is fully automated, i.e. the user can simply insert the processing rack containing the tissue sample into the processing container 18 in the processing chamber 13, connect the tubes, then use the control panel 14 to preset the steps to process the tissue sample. As discussed above, the processor unit 10 pumps the processing solutions and infiltration agent into and out of the processing container 18 at the proper time using pumps 24, 32. The user simply pushes a "start" button on the machine and can walk away as the tissue processes to completion. The processing unit 10 has a temperature probe that is adapted to communicate with the ohmic energy source and microwave energy source so that the energy sources turn on and off in relation to whether the actual temperature of the solution is below or above the target temperature. In an alternate embodiment, the present invention can be carried out manually, i.e. the user manually changes the reagent contents of the processing container 18 to complete the tissue processing.

Having thus described the invention in connection with the preferred embodiments thereof, it will be evident to those skilled in the art that various revisions can be made to the preferred embodiments described herein with out departing from the spirit and scope of the invention. It is my intention, however, that all such revisions and modifications that are evident to those skilled in the art will be included with in the scope of the following claims.

What is claimed is:

1. An apparatus for processing a tissue specimen with a series of solutions wherein the solutions contain a conductive agent, said apparatus comprising:
   a processing container inside the apparatus for receiving the solutions;
   electrodes powered by a power source and combined with the processing container, said electrodes for introducing ohmic energy into the solutions contained in the processing container; and
   a microwave energy generator combined with the apparatus for introducing microwave energy into the solutions contained in the processing container.

2. The apparatus of claim 1 wherein the solutions are stored in storage containers that are fluidly coupled to the processing container.

3. The apparatus of claim 1 further comprising a vacuum pump pneumatically combined with the processing chamber for creating less than atmospheric conditions inside the processing chamber.

4. The apparatus of claim 1 further comprising an infiltration agent reservoir adapted to be fluidly coupled with the processing container, said reservoir adapted to contain the infiltration agent, said reservoir further having a heating element for keeping the infiltration agent warm while in the reservoir.

5. The apparatus of claim 1 wherein the ohmic energy introduced across the solution is within a range of thirty (30) and three-thousand (3000) Hertz.

6. The apparatus of claim 1 further compositing a means for alternating the introduction of microwave energy and ohmic energy into the processing container so that both microwave and ohmic energy are not being introduced into the solutions at the same time.

7. The apparatus of claim 6 wherein duration of each cycle of ohmic energy is about one second.

8. The apparatus of claim 1 wherein the conductivity of the processing solutions is between 0.001 and 100 Siemens.

9. The apparatus of claim 1 wherein the solutions comprise green chemicals.

10. The apparatus of claim 1 wherein the conductive agent is Polyaniline.

11. An apparatus for processing a tissue specimen with a series of solutions wherein the solutions contain a conductive agent, said apparatus comprising:
    a processing container means for receiving the solutions, said container means adapted to be placed in the apparatus;
    said solutions for fixing, dehydrating, clearing, and impregnating said tissue specimen;
    an electrode means powered by a power source and combined with the processing container, said electrode means for introducing ohmic energy into the solutions contained in the processing container; and
    a microwave energy generating means for introducing microwave energy into the solutions contained in the processing container.

12. An apparatus for processing a tissue specimen with a series of solutions wherein the solutions comprise a conductive agent, said apparatus comprising:
    a processing container inside the apparatus for receiving the solutions;
    electrodes powered by a power source and combined with the processing container, said electrodes for introducing ohmic energy into the solutions contained in the processing container; and
    a microwave energy generator combined with the apparatus for introducing microwave energy into the solutions contained in the processing container;
    wherein microwave energy and ohmic energy are introduced into the processing container in an alternating fashion so that both microwave and ohmic energy are not being introduced into the container and its contents at the same time.

* * * * *